(12) United States Patent
Vellaisamy et al.

(10) Patent No.: US 11,660,004 B2
(45) Date of Patent: May 30, 2023

(54) SYSTEM, DEVICE AND SENSOR FOR MONITORING CIRCULATORY CONDITIONS AND A METHOD FOR MANUFACTURING THE SAME

(71) Applicant: City University of Hong Kong, Kowloon (HK)

(72) Inventors: A. L. Roy Vellaisamy, Kowloon (HK); Qijun Sun, Kowloon (HK); Jiaqing Zhuang, Kowloon (HK)

(73) Assignee: City University of Hong Kong, Kowloon (HK)

( * ) Notice: Subject to any disclaimer, the term of this patent is extended or adjusted under 35 U.S.C. 154(b) by 473 days.

(21) Appl. No.: 16/344,137

(22) PCT Filed: Oct. 27, 2016

(86) PCT No.: PCT/CN2016/103548
§ 371 (c)(1),
(2) Date: Apr. 23, 2019

(87) PCT Pub. No.: WO2018/076232
PCT Pub. Date: May 3, 2018

(65) Prior Publication Data
US 2020/0060554 A1    Feb. 27, 2020

(51) Int. Cl.
*A61B 5/02* (2006.01)
*A61B 5/00* (2006.01)

(52) U.S. Cl.
CPC ............ *A61B 5/02* (2013.01); *A61B 5/742* (2013.01); *A61B 2562/12* (2013.01); *A61B 2562/164* (2013.01)

(58) Field of Classification Search
CPC ..... A61B 5/02; A61B 5/021; A61B 2562/164; A61B 5/742; A61B 2562/12
USPC ....................................................... 600/481
See application file for complete search history.

(56) References Cited

U.S. PATENT DOCUMENTS

| | | | |
|---|---|---|---|
| 10,439,517 B2 * | 10/2019 | Wang | H02N 1/04 |
| 2006/0178589 A1 * | 8/2006 | Dobak, III | A61B 7/00 600/514 |
| 2016/0011063 A1 * | 1/2016 | Zhang | A61B 5/11 600/301 |

FOREIGN PATENT DOCUMENTS

| | | | |
|---|---|---|---|
| CN | 104257366 A | * | 1/2015 |
| CN | 104257366 A | | 1/2015 |
| CN | 105741980 A | | 7/2016 |

* cited by examiner

*Primary Examiner* — Daniel L Cerioni
(74) *Attorney, Agent, or Firm* — Renner Kenner Greive Bobak Taylor & Weber

(57) ABSTRACT

A system and method of a sensor for monitoring a circulatory condition, the system including a layered structure having a graphite-composite bonded to a flexible substrate, wherein the sensor further includes a microstructure arranged to increase the sensitivity of the sensor.

14 Claims, 6 Drawing Sheets

SYSTEM, DEVICE AND SENSOR FOR MONITORING CIRCULATORY CONDITIONS AND A METHOD FOR MANUFACTURING THE SAME

FIELD OF INVENTION

The present invention is directed to a system, device and sensor for monitoring circulatory conditions and a method for manufacturing the same. In particular, embodiments of the system, device and sensor are arranged to monitor blood pressure and pulse.

BACKGROUND

Blood pressure is a fundamental marker of human (and animal) health and is a useful marker for determining any one of a number of medical conditions and diseases. It is a fundamental marker for doctors and health care professionals when attempting to diagnose the health of a patient.

It is particularly useful to monitor a person's blood pressure and heart beat in real time in an ongoing, continuous manner. However, existing blood pressure measurement devices have a number of drawbacks.

Firstly, blood pressure measurement devices which are capable of ongoing monitoring of a person's blood pressure are generally large, bulky and heavy, making them difficult or inconvenient to carry or transport to other locations.

Secondly, blood pressure monitors continue to be difficult to use for novices and non-medical professionals. It is difficult for a person to measure their blood pressure without assistance.

Lastly, existing products are expensive and therefore not suitable for casual use.

SUMMARY OF INVENTION

In a first aspect, the present invention provides a sensor for monitoring circulatory conditions comprising a layered structure having a graphite-composite bonded to a flexible substrate, wherein the sensor further includes a microstructure arranged to increase the sensitivity of the sensor.

The sensor may further include at least two layers of the layered structure formed in a laminate.

The sensor may also include at least one conductive wire electrically connected to the layered structure.

The graphite composite may be a graphite-polydimethylsiloxane (PDMS) composite.

The flexible substrate may be an indium tin oxide (ITO) coated polyethylene terephthalate (PET).

In one embodiment, the microstructure is a granular material, such as a silicon based sand.

In a second aspect, the present invention provides a device incorporating a sensor in accordance with a first aspect of the invention.

In a third aspect, the present invention provides a system incorporating a device in accordance with a first aspect of the invention. The device may include a display unit and/or an external communication means.

In a fourth aspect, the present invention provides a method of manufacturing a sensor, comprising the steps of, placing a graphite composite solution onto a flexible substrate, and subsequently forming a microstructure within the graphite composite solution to form a sensor including a microstructure.

The flexible substrate may be an indium tin oxide (ITO) coated polyethylene terephthalate (PET). The composite solution may be a graphite-polydimethylsiloxane (PDMS) composite.

The method may further comprise an annealing step.

The method may comprise the further step of forming the microstructure by placing a piece of sand paper on top of the wet firm to form the microstructure.

The method may comprise the further step of laminating at least two pieces of film and incorporating a copper wire attached to the ITO to form an electrical connection.

The method may comprise the further step of preparing a graphite-polydimethylsiloxane (PDMS) composite by mixing graphite powder with a PDMS solution.

BRIEF DESCRIPTION OF THE DRAWINGS

The present invention is described by way of non-limiting examples within the following description and figures.

DETAILED DESCRIPTION

Broadly speaking, an embodiment of the present invention a sensor for monitoring a circulatory condition, such as blood pressure and/or pulse (heart rate). Broadly, the sensor comprises a layered structure having a graphite-composite bonded to a flexible substrate, wherein the sensor further includes a microstructure arranged to increase the sensitivity of the sensor. In one embodiment, the sensor includes at least two layers of the layered structure formed in a laminate and further includes at least one conductive wire electrically connected to the layered structure.

As will be described below, in one exemplary embodiment, the graphite composite is a graphite-polydimethylsiloxane (PDMS) composite and the flexible substrate is an indium tin oxide (ITO) coated polyethylene terephthalate (PET). Moreover, in the embodiment described, the microstructure is a granular material, such as a silicon based sand.

Figure 1A:
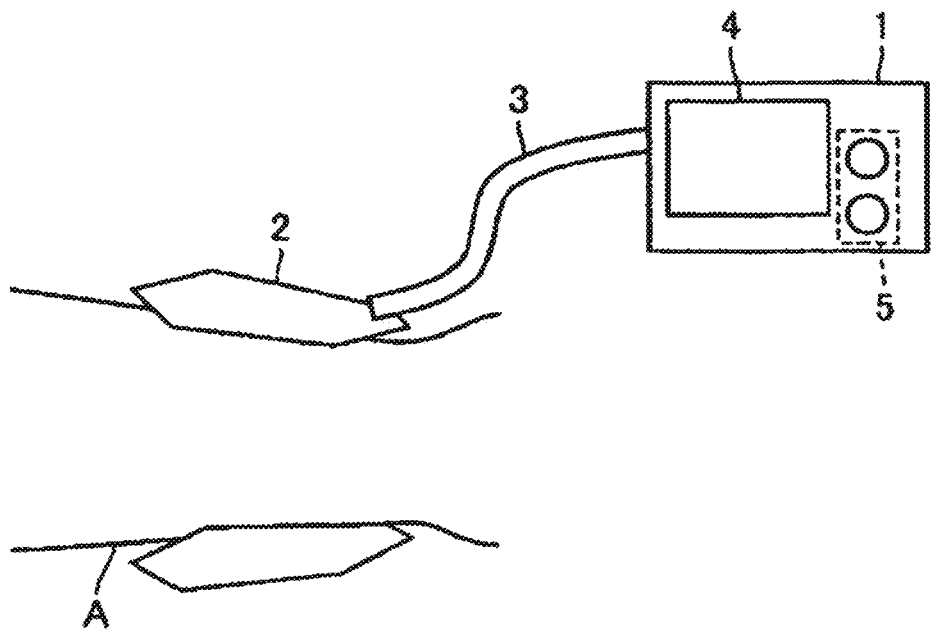
FIGS. 1a and 1b are schematic diagrams illustrating a device in accordance with an embodiment of the invention.

Referring now to FIG. 1a, there is shown a device incorporating a sensor according to one embodiment of the present invention. The device 1 includes a cuff (incorporating a sensor in accordance with an embodiment of the invention) 2, and measures blood pressure and pulse rate of a person by placing cuff 2 wrapped around a wrist A of the measurement subject.

It will be understood that the measurement site for blood pressure and pulse rate is not limited to the wrist, but may be any suitable place where a vein or artery (blood vessel) is located, such as anywhere on the arm, anywhere on the hand, anywhere on the leg, or any other suitable area where a volume of an artery can be detected.

The device 1 is arranged on a front surface with a display 4 and an operation panel 5 with a plurality of operation buttons. The device 1 also includes a cord 3 for connecting the device 1 and the cuff 2.

It will be understood that the device 1 as described with reference to FIG. 1a is merely an example of the type of device that may incorporate a sensor in accordance with an embodiment of the invention, and obvious variations to any one or more of the features described above are contemplated.

Figure 1B:
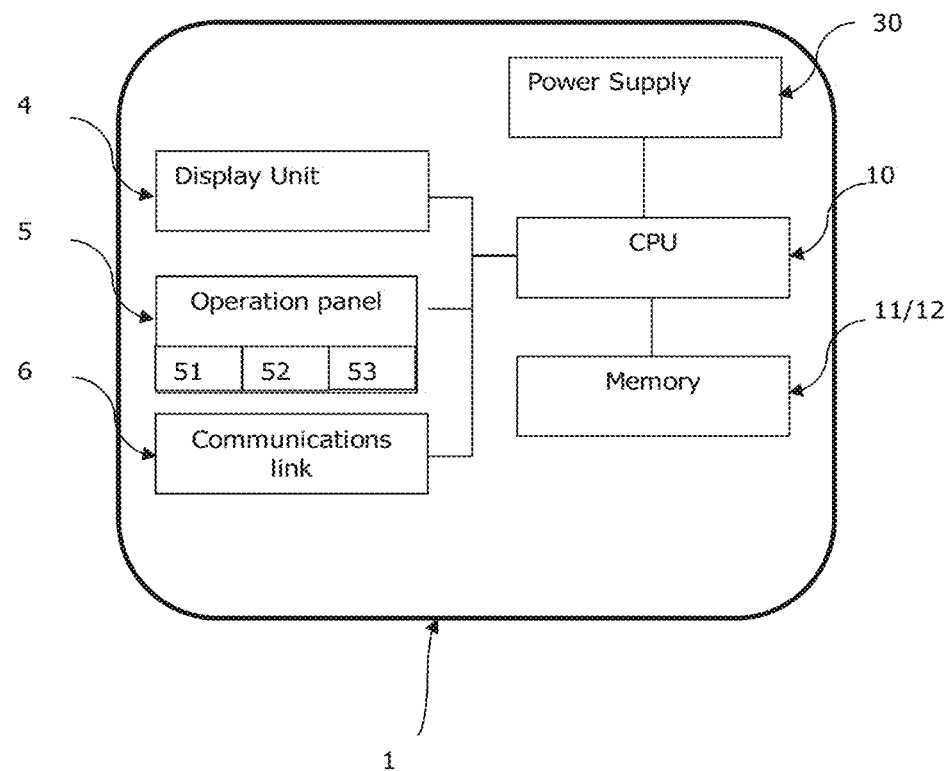

FIG. 1b is a view schematically showing a hardware configuration of the device 1. The device 1 includes, in addition to the display 4 and the operation panel 5 discussed above, a CPU (Central Processing Unit) 10 for controlling the operation of the device 1, memory 11 functioning in accordance with instructions issued by the CPU 10, a memory 12 for storing information, a communications link 6 (which may be wired or wireless, such as USB, Bluetooth, WiFi, etc.), and a power supply 30 for supplying power to the CPU 10. The operation panel 5 includes a power switch 51 operated to switch ON/OFF of the power supply with respect to the device 1, a measurement switch 52 operated to cause the device 1 to start the measurement of the blood pressure and/or pulse rate, a stop switch 53 operated to cause the device 1 to stop the measurement operation.

The device 1 may form part of a larger system incorporating the device. That is, the device may communicate with one or more computing systems or computing networks (not shown) to distribute collected data to other systems. Such variations are within the purview of a person skilled in the art.

It will also be understood that the embodiments described with regard to FIGS. 1a and 1b are exemplary embodiments and additional features may be incorporated into the device 1, as would be known to a person skilled in the art. The device 1 is intended to be illustrative and not restrictive.

Figure 1C:
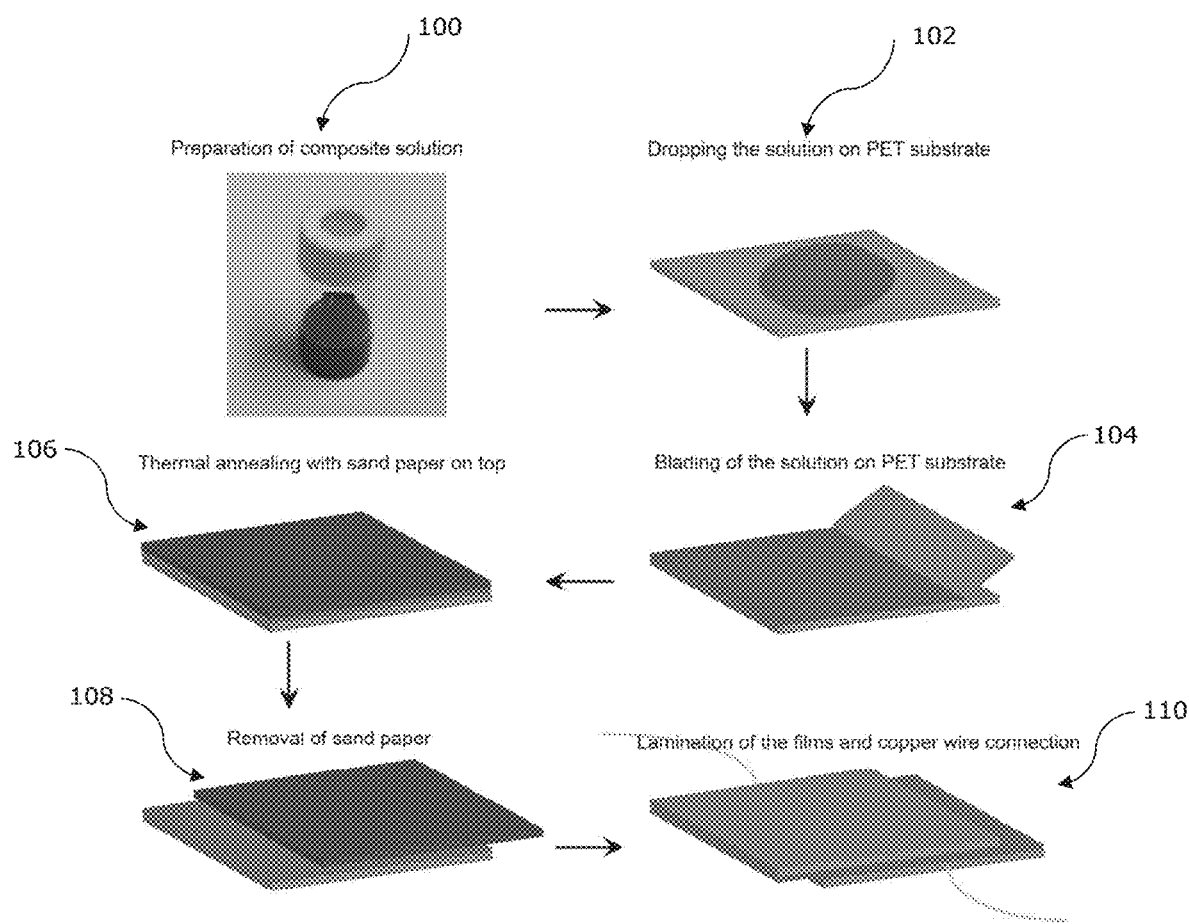
FIG. 1c is a diagram illustrating a flow chart for a fabrication process for a sensor in accordance with an embodiment of the invention.

Referring to FIG. 1c, there is shown a flow chart for a fabrication process for a sensor in accordance with an embodiment of the invention.

In the embodiment illustrated, the sensor is a resistive sensor. That is, the sensor is made of a material with a variable electrical resistance. As the material is compressed and/or flexed, the resistance of the material changes temporarily during the period of time that the sensor is flex and/or deformed.

Turing to FIG. 1c, there is shown, at step 100, the preparation of a graphite-polydimethylsiloxane (PDMS) composite by mixing graphite powder with a PDMS solution.

At step 102, the composite solution is placed (i.e. "dropped") on a flexible indium tin oxide (ITO) coated polyethylene terephthalate (PET) substrate. ITO-coated PET films are commercially available and preparation of the surface is consistent with standard procedure, as would be understood by the skilled addressee. At step 104, the solution is then "bladed" (i.e. spread across the entire surface to form a film of substantially even thickness).

At step 106 a piece of sand paper is placed on top of the wet film to form a microstructure on top of the film. This step is followed by a thermal annealing step in ambient conditions. The microstructure on top of the film acts to further improve the sensitivity of the sensor.

The composite film is tailed into pieces and at step 108, two pieces of the film are laminated with a copper wire attached to the ITO, to form the finished sensor.

Figure 2:
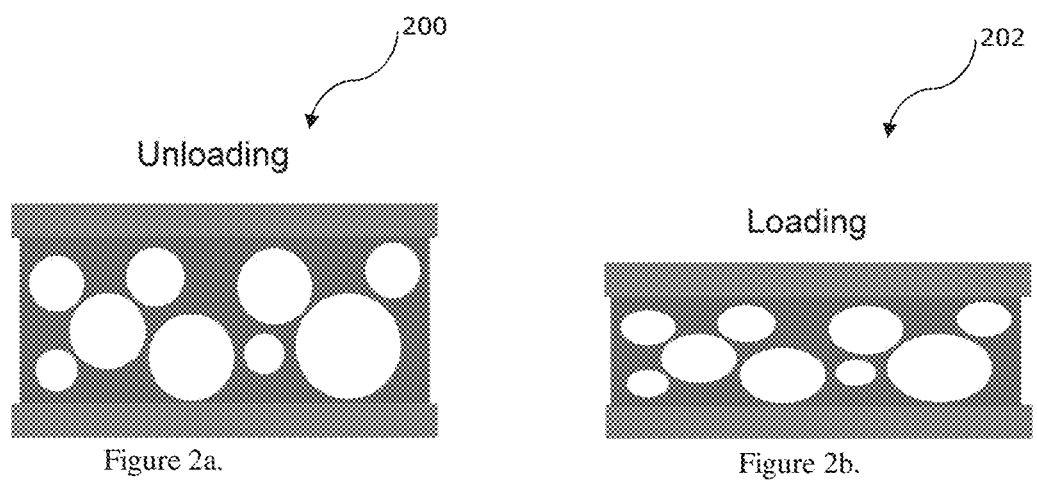
FIGS. 2a and 2b are diagrammatical representations of the working mechanism of the sensor of FIG. 1a or FIG. 1b.

The sensitivity of the piezo-resistive pressure sensor depends on the mechanical properties of the conducting composite films. Referring to FIG. 2, there is shown diagrammatical representations of the working mechanism of the graphite-PDMS composite based pressure sensor.

The composite film deforms as show in FIG. 2 at 202 and returns to its initial state (as shown in FIG. 2 at 200) when loading and unloading sensor with an appropriate amount of pressure, resulting in a resultant decrease and increase of the resistance of the device, respectively. The resistance change depends on the pressure applied to the sensor by an external force. The sensitivity of the sensor is such that the expansion and contraction of a vein and/or artery of a person is sufficient to cause a discernable and easily measureable change in current flow through the sensor. In other words, the resultant sensor is sensitive enough to detect a wrist pulse and the blood pressure of a user.

Figure 3A:
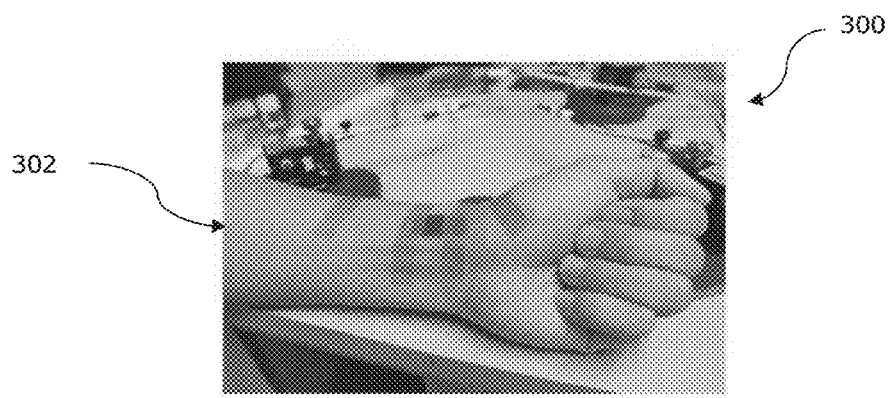
FIG. 3a is an image of the sensor of FIG. 1a or FIG. 1b in situ on the wrist of a person.
Figure 3B:
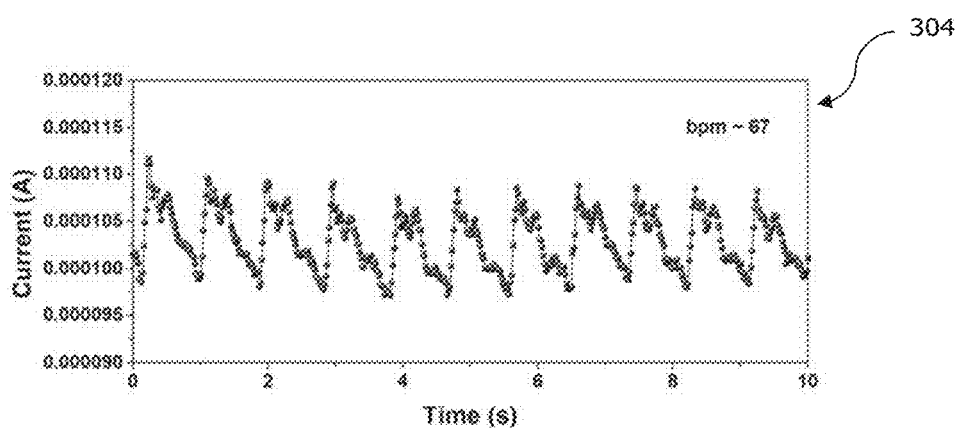
FIG. 3b is a graph illustrating a plot of data gathered from the sensor of FIG. 3a as a function of current versus time.

With reference to FIGS. 3a and 3b, there is shown the collection of pulse information from a sensor in accordance with an embodiment of the invention. In particular, at FIG. 3a, there is shown a sensor 300 attached to the arm of a user 302 with the use of appropriate adhesive tape. It will be understood that the embodiment shown in FIG. 3a is provided for illustration purposes only, and the use of adhesive tape is one of a number of ways in which the sensor 300 may be attached, either temporarily or semi-permanently.

Referring to FIG. 3b, there is shown a graph 304 illustrating the change in current (in Amps) which flows through the sensor 300 as the users pulse changes over time. As can be seen from the graph 304 and in particular the line, the current flowing through the resistor changes in real time in a manner which clearly "maps" the pulse of the user.

This principle is more clearly illustrated with reference to FIGS. 4a and 4b. At FIG. 4a, there is shown a schematic diagram of a pressure sensor on the arm of a user. As depicted in FIG. 4b, when the arm is in relaxed state 400 (state 1), the blood flows in a manner that prevents any "inflation" (movement) of the vein or artery, resulting in a pressure between the skin and pressure sensor that is very gentle. In turn, with reference to FIG. 4c, a small current is generated as shown at 408 in FIG. 4c (State 1).

Figure 4A:
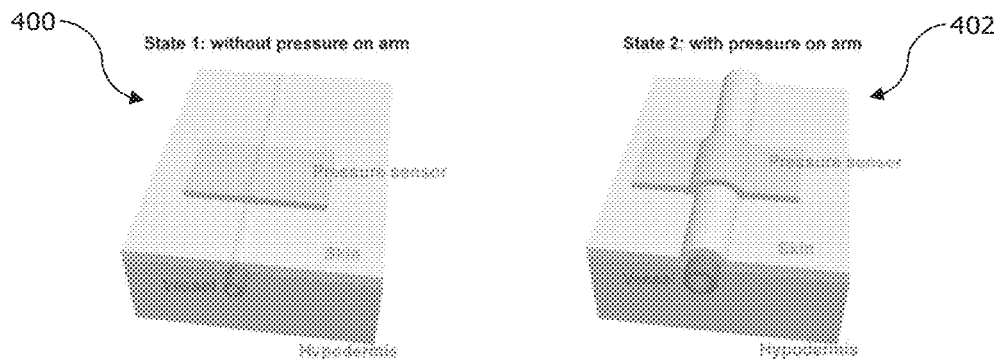
FIG. 4a is a schematic diagram illustrating the sensor of FIG. 1a, FIG. 1b or FIG. 1c in situ on the skin of a person.
Figure 4B:
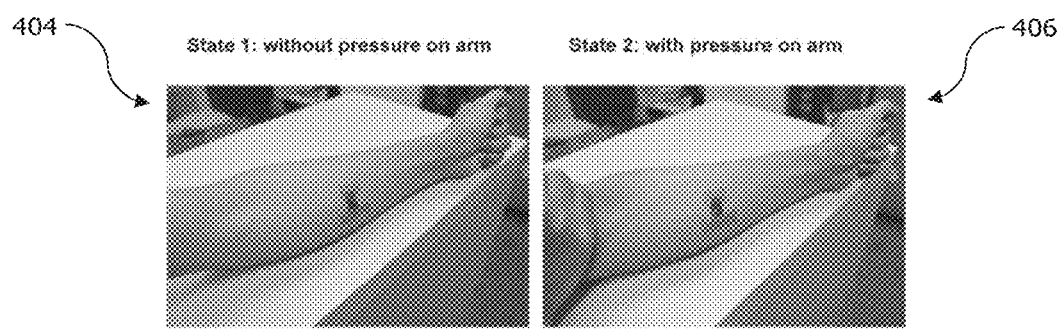
FIG. 4b is an image of the sensor of FIG. 1a, FIG. 1b or FIG. 1c in situ on the arm of a person.

In contrast, as shown in FIG. 4b, when a user clenches their arm to cause their veins to "pop" (i.e. create a temporary excess of blood in the vein to cause the vein to temporarily enlarge) as shown at 402 and 406 at FIGS. 4a and 4b respectively. In other words, clenching you pressed arm blocks the blood flow, which increases the pressure.

Figure 4C:
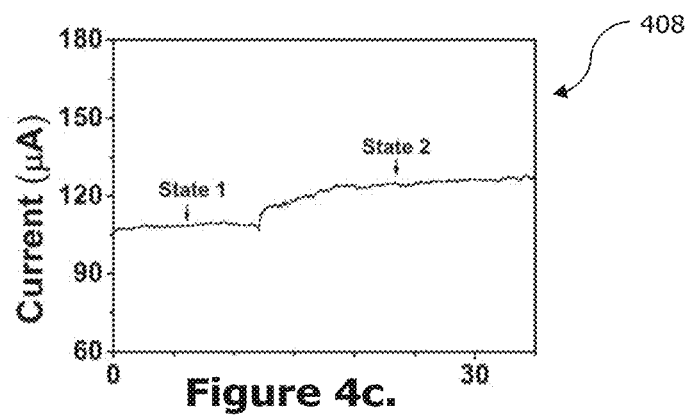
FIG. 4c is a graph illustrating a real time measurement of data collected from the sensor of FIG. 1a, FIG. 1b or FIG. 1c.

As depicted in FIG. 4a and FIG. 4b, when the arm is in relaxed state (state 1), the blood flows fluently and the pressure between the kin and pressure sensor is very gentle, which results in a small current as shown in FIG. 4c (State 1). However, as shown in FIG. 4b, the pressed arm blocks the blood flow, which increases the pressure between the arm and the pressure sensor, leading to a large current as shown in FIG. 4c (State 2). So, the blood pressure can be detected easily.

Advantages

The embodiments described herein provide a novel means of monitoring circulatory conditions, which is ideally suited for situations where traditional, heavy, expensive monitors are not available. The embodiments provide this advantage, in part, due to the novel pressure sensor design which occupies little space, yet is robust due to its flexibility and long life stability.

Additionally, embodiments described herein provide a highly accurate sensor where the detection limit of the sensor is as low as several Pascal. As described herein, detection is reliable and highly reproducible, making the sensor highly attractive for small portable devices which are to be used by non-expert users.

As the device and sensor have a low power consumption, the device can be powered by conventional battery technology.

A further advantage of the embodiment is the use of low cost materials to fabricate the sensor (thereby reducing cost) and also the relatively simple fabrication method (which also reduces cost when compared to known sensors).

Although not required, the embodiments described with reference to the Figures can be implemented to file an application programming interface (API) or as a series of libraries for use by a developer or can be included within another software application, such as a terminal or personal computer operating system or a portable computing device operating system. Generally, as program modules include routines, programs, objects, components and data files the skilled person assisting in the performance of particular functions, will understand that the functionality of the software application may be distributed across a number of routines, objects or components to achieve the same functionality.

It will be appreciated by persons skilled in the art that numerous variations and/or modifications may be made to the present invention as shown in the specific embodiments without departing from the spirit or scope of the invention as broadly described. The present embodiments are, therefore, to be considered in all respects as illustrative and not restrictive. It will also be appreciated by persons skilled in the art that the present invention may also include further additional modifications made to the device which does not affect the overall functioning of the device.

It will also be appreciated that where the methods and systems of the present invention are either wholly implemented by computing system or partly implemented by computing systems then any appropriate computing system architecture may be utilized. This will include stand-alone computers, network computers and dedicated hardware devices. Where the terms "computing system" and "computing device" are used, these terms are intended to cover any appropriate arrangement of computer hardware capable of implementing the function described.

Any reference to prior art contained herein is not to be taken as an admission that the information is common general knowledge, unless otherwise indicated. It is to be understood that, if any prior art information is referred to herein, such reference does not constitute an admission that the information forms a part of the common general knowledge in the art, any other country.

The invention claimed is:

1. A sensor for monitoring a circulatory condition, comprising a layered structure including at least two layers formed into a laminate; each of said at least two layers comprising a graphite-composite bonded to a flexible substrate; the graphite composite having a sandpaper microstructure impacting a sensitivity of the sensor; the sandpaper microstructure being formed by placing a piece of sandpaper on top of a wet film of a solution of the graphite composite and annealing the wet film to form an annealed film having the sandpaper microstructure, and wherein the sensor is adapted to detect expansion and contraction of a vein and/or artery of a person and in turn cause a measurable change in current flow through the sensor.

2. The sensor in accordance with claim 1, further including at least one conductive wire electrically connected to the layered structure.

3. The sensor in accordance with claim 1, wherein the graphite composite is a graphite-polydimethylsiloxane (PDMS) composite.

4. The sensor in accordance with claim 1, wherein the flexible substrate is an indium tin oxide (ITO) coated polyethylene terephthalate (PET).

5. A device incorporating a sensor in accordance with claim 1.

6. The device in accordance with claim 5, further including a display unit.

7. The device in accordance with claim 6, further including an external communication means.

8. A system incorporating a device in accordance with claim 5.

9. A method of manufacturing a sensor, comprising the steps of forming at least two annealed films, each film formed by:
   a. placing a graphite composite solution onto a flexible substrate,
   b. subsequently forming a sandpaper microstructure from the graphite composite solution by placing a piece of sandpaper on top of a wet film of the graphite composite solution and annealing the wet film to form an annealed film including the sandpaper microstructure; and
   c. laminating the at least two annealed films; and wherein the sensor is adapted to detect expansion and contraction of a vein and/or artery of a person and in turn cause a measurable change in current flow through the sensor.

10. The method in accordance with claim 9, wherein the flexible substrate is an indium tin oxide (ITO) coated polyethylene terephthalate (PET).

11. The method in accordance with claim 9, wherein the graphite composite solution is a graphite-polydimethylsiloxane (PDMS) composite.

12. The method in accordance with claim 10, comprising the further step of incorporating a copper wire attached to the ITO to form an electrical connection.

13. The method in accordance with claim 9, wherein the graphite-polydimethylsiloxane (PDMS) composite is formed by mixing graphite powder with a PDMS solution.

14. The sensor in accordance with claim 1, wherein the sensor is adapted to detect a wrist pulse and a blood pressure of a user.

* * * * *